United States Patent

Bruhin

[11] Patent Number: 5,877,353
[45] Date of Patent: Mar. 2, 1999

[54] PROCESS FOR THE PREPARATION OF BENZOPHENONE DERIVATIVES

[75] Inventor: Jürg Bruhin, Basel, Switzerland

[73] Assignee: Hoffmann-La Roche Inc., Nutley, N.J.

[21] Appl. No.: 7,612

[22] Filed: Jan. 15, 1998

[30] Foreign Application Priority Data

Jan. 22, 1997 [EP] European Pat. Off. ............... 97100930

[51] Int. Cl.⁶ .................................................. C07C 49/84
[52] U.S. Cl. .......................... 568/333; 568/332; 568/763; 514/355
[58] Field of Search ..................................... 568/332, 333, 568/763; 514/355

[56] References Cited

U.S. PATENT DOCUMENTS 5,236,952  8/1993  Bernauer et al. .
5,389,653  2/1995  Bernauer et al. .
5,476,875  12/1995  Bernauer et al. .
5,633,371  5/1997  Bernauer et al. .

FOREIGN PATENT DOCUMENTS 273 528  7/1988  European Pat. Off. .

OTHER PUBLICATIONS

Borgulya, et al. Drugs of the Future (1991) 16, pp. 719–721.
Borgulya, et al. Helvetica Chimica Acta (1989), 72, pp. 952–968.

Acta Chimica Scandinavica, vol. 8, 1954 pp. 1519–1529.
Abstract corresponding to (C1) Acta Chimica Scandinavica, vol. 8, 1954 pp. 1519–1529.

*Primary Examiner*—Gary Geist
*Assistant Examiner*—S. Padmanabhan
*Attorney, Agent, or Firm*—George W. Johnston; Patricia S. Rocha-Tramaloni; Robert A. Silverman

[57] ABSTRACT

The present invention relates to a process for the preparation of benzophenone derivatives and comprises a selective crystallization of alkali salts of compounds of formula (I)

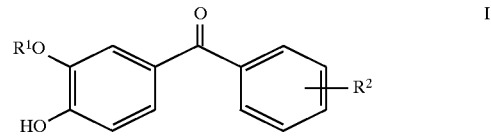

wherein $R^1$ is lower-alkyl and $R^2$ is hydrogen, lower-alkyl or halogen,
from the isomeric alkali salts of the 3-hydroxy compounds of formula (II),

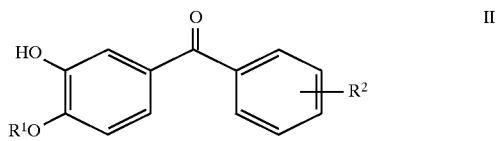

wherein $R^1$ and $R^2$ are as defined above.

12 Claims, No Drawings

PROCESS FOR THE PREPARATION OF BENZOPHENONE DERIVATIVES

BACKGROUND OF THE INVENTION

Benzophenones such as 3,4-dihydroxy-4'-methyl-5-nitrobenzophenone (U.S. Pat. Nos. 5,236,952, 5,389,653, 5,476,875 and 5,563,371) are known catechol-O-methyltransferase (COMT) inhibitors and are especially suitable for the therapy of Parkinson's disease and for the treatment of depressions and similar disease states.

Synthesis of 3,4-dihydroxy-4'-methyl-5-nitrobenzophenone (see U.S. Pat. No. 5,236,952, 5,389,653, 5,476,875 and 5,563,371 and Borgulya et al., Drugs of the Future (1991) 16, 719–721) is exemplary of benzophenone type COMT inhibitor synthesis.

The synthesis is based essentially on the reaction of 4-bromotoluene with 4-(benzyloxy)-3-methoxybenzaldehyde in the presence of butyllithium to give 4-(benzyloxy)-3-methoxy-4'-methylbenzhydrol. By oxidation to 4-(benzyloxy)-3-methoxy-4'-methylbenzophenone and subsequent debenzylation there is obtained 4-hydroxy-3-methoxy-4'-methylbenzophenone. After regioselective nitration to 4-hydroxy-3-methoxy-4'-methyl-5-nitrobenzophenone and subsequent hydrolysis of the methoxy group there is obtained the aforementioned inhibitor 3,4-dihydroxy-4'-methyl-5-nitrobenzophenone.

The above mentioned synthesis of other analogous catechol-O-methyltransferase inhibitors is described by Borgulya et al. (Helvetica Chimica Acta (1989) 72, 952–968), for example there are described analogous compounds which have an unsubstituted phenyl ring.

This known synthetic route, and similar synthetic routes for related benzophenones, has considerable disadvantages, which are primarily associated with the high number of steps of the synthesis and the time/apparatus expenditure associated therewith. Moreover, relatively expensive starting materials, such as vanillin and 4-bromotoluene, are required for this synthetic route.

Surprisingly, it has now been found that these disadvantages can be largely avoided by subjecting a compound of formula (III) and a reactive acid derivative of formula (IV) to a Friedel-Crafts acylation, cleaving off one of the two substituents $R^1$ and separating the resulting salts of compounds of formula (I) from the isomeric salts of compounds of formula (II) according to one of the processes described below.

SUMMARY OF THE INVENTION

The present invention relates to a process for the manufacture of benzophenone derivatives which are useful intermediates in the production of pharmaceutically active benzophenones such as 3,4-dihydroxy-4'-methyl-5-nitrobenzophenone.

The process is based on the separation of an alkali salt of the 4-hydroxy compound of formula (I),

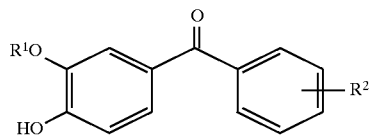

wherein $R^1$ is lower-alkyl and $R^2$ is hydrogen, lower-alkyl or halogen,
from the isomeric alkali salt of the 3-hydroxy compound of formula (II),

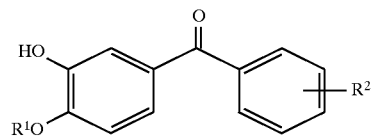

wherein $R^1$ and $R^2$ are as defined above.

Specifically, the present invention is a process for selective crystallization of a compound of formula (I),

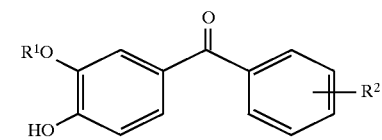

wherein $R^1$ is lower-alkyl and $R^2$ is hydrogen, lower-alkyl or halogen,
from an aqueous solution containing a mixture of potassium salts of compounds of formula (I) and of formula (II)

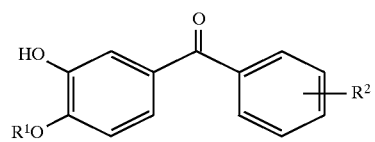

wherein $R^1$ and $R^2$ are as defined above
by adding sodium or lithium salts to the mixture of potassium salts to crystallize the compound of formula (I), and isolating the compound of formula (I) in crystalline form as a sodium or lithium salt. In preferred processes, $R^2$ is in the para position. $R^1$ and $R^2$ may be methyl, and the salt may be one or more salts, particularly a lithium or sodium salt. The process may additionally include separating the compound of formula (I) in crystalline form from the sodium or lithium in order to obtain the compound in soluble form.

This invention also includes a process for making a compound of formula (I) in crystalline form by combining a compound of formula (III),

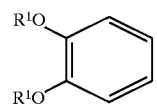

wherein $R^1$ is as defined as above, with a reactive acid derivative of formula (IV)

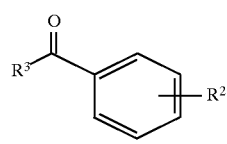

wherein $R^2$ is as defined above and $R^3$ is halogen, under conditions suitable for a Friedel-Crafts acylation, and exposing the resulting product to conditions under which the substituent $R^1$ is cleaved off, and extracting with a potassium salt, to obtain a solution containing a mixture of the potassium salts of the compounds of formula (I) and formula (11), then adding a lithium or sodium salt to the solution to crystallize the compound of formula (I), and isolating the compound of formula (I) in crystalline form as a sodium or lithium salt. This process may also include separating the compound of formula (I) in crystalline form from the sodium or lithium in order to obtain the compound in soluble form. Aluminum trichloride is a preferred reagent to be added to effect the Friedel-Crafts acylation, the cleavage, or both. A preferred $R^3$ is chlorine, and methyl is preferred for $R^1$ and $R^2$, in particular where $R^2$ is in the para position.

Another process of this invention is a process for making compounds of formula (VI)

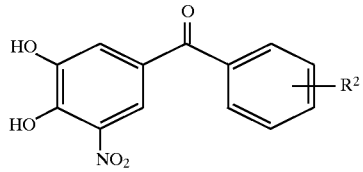

VI wherein $R^2$ is hydrogen, lower-alkyl or halogen by adding nitric acid to a compound of formula (I) to obtain a compound of formula (V),

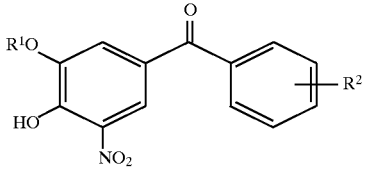

V wherein $R^1$ and $R^2$ are as defined above, and converting $R^1$ to hydroxy to obtain a compound of formula (VI),

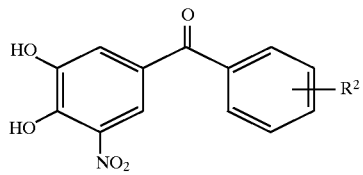

VI wherein $R^2$ is as defined above. Methyl is preferred for $R^1$ and $R^2$.

Compounds of formula (I) are important intermediates for the manufacture of pharmaceutically active compounds, for example for the manufacture of 3,4-dihydroxy-4'-methyl-5-nitrobenzophenone, 3,4-dihydroxy-5-nitrobenzophenone or 3,4-dihydroxy-4'-chloro-5-nitrobenzophenone.

DETAILED DESCRIPTION OF THE INVENTION

Accordingly, the benzophenone derivative compounds of formula (I) are produced by a process whereby the salts of the compounds of formula (I) are separated from the salts of the corresponding isomeric compounds of formula (II),

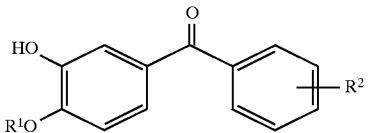

II wherein $R^1$ and $R^2$ are as defined above,
by selective crystallization. Surprisingly, the sodium or lithium of compounds of formula (II) have a far better solubility than the corresponding salts of the compounds of formula (I), thus sodium or lithium salts may be added to a mixture of the compounds to bring about selective crystallization.

The selective crystallization of Na and Li salts of compounds of formula (I) from a solution of a mixture of salts of compounds of formula (I) and formula (II) provides highly effective separation of these isomeric compounds, due to the discovery that the Na and Li salts of compounds of formula (II) remain soluble in conditions where corresponding salts of compounds of formula (I) form crystals. A typical mixture will contain the isomers in a ratio of about 70-80:15 30-20.

The relative solubility of the isomers can be exploited by crystallization, where water or water-containing solvent mixtures are used as the solvent for the crystallization. Aqueous salt solutions are preferred solvents for the selective crystallization. The isomeric compounds of formulae (I) and (II) are preferably extracted from an organic phase with an aqueous potassium hydroxide solution. To the aqueous phase there can be added most preferably a saturated aqueous sodium chloride solution. Thereby, the sodium salt of the corresponding compound of formula (I) crystallizes out, while the corresponding sodium or potassium salt of the isomer of formula (II) remains in solution.

Accordingly, depending on the salt added, what is obtained are the sodium (or lithium) salts of a compound of formula (I). Both Na and Li may be added together to obtain a combination of Na and Li salts of the compound of formula (I).

If the corresponding potassium salts of compounds of formulae (I) and (II) are already in aqueous solution, then the Na or Li can be directly added to bring about selective crystallization. If the compounds formulae (I) and (II) are in an organic phase (for example, after their synthesis by the Friedel-Craft acylation), they can be extracted from the organic phase with an alkali hydroxide solution, for example a potassium hydroxide solution, after which the separation is performed in the aqueous phase. Specifically, to the aqueous potassium hydroxide phase there can be added, for example, a saturated aqueous sodium chloride solution. Thereby, the sodium salt of the compound of formula (I) crystallizes out, while the sodium or potassium salt of the isomer of formula (II) remains in solution.

The crystalline form of the compound of formula (I) may be separated from the lithium or sodium to be obtained in soluble form, using methods which will be known to a skilled person. For example, the Li or Na salt of the compound can be washed with an aqueous dilute solution of the same salt. By "dilute" is meant a concentration of no more than 15%. Once so purified, the compound of formula (I) can be transferred by acidification, preferably with dilute acid, and extraction with an organic solvent. This is useful for subsequent processing of the compound of formula (I) to make the final benzophenone product as further described below. Where desired, the compound of formula (I) can also be purified further according to known methods. Thus for example the precipitated sodium salt can be separated and subsequently washed e.g. with a dilute, aqueous sodium chloride solution. The thus-purified salt of formula (I) can then be transferred into an organic phase by acidification, e.g. with dilute hydrochloric acid, and extraction with an organic solvent, e.g. ethyl acetate.

The amounts or concentrations of Li or Na to be added to bring about selective crystallization will be readily determined by a skilled person. For example, it will be visible when a sufficient amount of salt has been added to cause the salt of the compound of formula (I) to precipitate in crystalline form. Solvents containing concentrations of solute which are standard for crystallization/precipitation of salts may be used. The preferred salt is sodium, although lithium is also useful. The anion may be a water soluble anion such as hydroxide or a halogen, preferably chlorine. The most preferred salt is sodium chloride.

The substituent $R^2$ can be situated in the ortho-, meta- and para-position. In a preferred embodiment it is situated in the para-position. Especially preferred processes are those in which compounds in which $R^1$ and $R^2$ represent methyl groups are used.

The term "lower-alkyl" used for the definition of the general formulae relates to straight-chain or branched alkyl groups which contain a maximum of eight, preferably a maximum of four, carbon atoms. The term embraces, for example, methyl, ethyl, n-propyl, isopropyl, n-butyl, isobutyl, sec.butyl, tert.butyl, pentyl, hexyl and the like. The term "halogen" stands for fluorine, chlorine, bromine and iodine.

In order to obtain a solution containing a mixture of the compounds of formulae (I) and (II), a process of this invention can be used. The process begins by reacting a compound of formula (III),

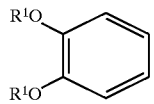   III wherein $R^1$ is lower-alkyl,
with an activated acid derivative, e.g. with a reactive acid derivative of formula (IV)

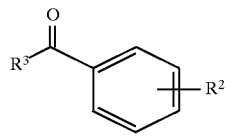   IV wherein $R^2$ is as defined above and $R^3$ is halogen, preferably chlorine, under Friedel-Crafts acylation conditions. Compounds of formulae III and IV are well known commodities. The Friedel-Crafts acylation is a standard reaction which will be known to a person skilled in the art. Thus a skilled person will readily determine suitable reagents and conditions to accomplish this reaction. In the reaction an aromatic ketone is formed by the reaction of the aromatic compound with an acylating agent under the influence of a Friedel-Crafts catalyst. The reaction of a compound of formula (III) with a compound of formula (IV) is described in detail in Example 1. The result of the Friedel-Crafts reaction is the formation of the compound of formula VII (see below). To obtain the mixture, one of the two lower-alkyl ether bonds $R^1$—O— is subsequently cleaved from the compound of formula (VII). This cleavage may be effected with reagents and conditions for hydrolyzing ether bonds which will be known to a skilled person. The resulting solution will contain an amount of the two isomers in the ratio of 70-80:30-20. The solution may be extracted with a potassium salt in order to obtain a solution containing a mixture of potassium salts of the two isomers.

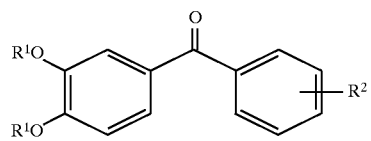   VII wherein $R^1$ and $R^2$ are as defined above.

One particularly convenient acylating agent is aluminum trichloride, although other conventional agents may also be used. When the Friedel-Crafts acylation is carried out with aluminium trichloride, the subsequent cleavage may also conveniently effected by the addition of aluminium trichloride. The isomers of formulae (I) and (II) which result from the cleavage can then be separated as described above.

Accordingly, the present invention includes a process for the manufacture of benzophenone derivatives characterized by subjecting a compound of formula (III) and a reactive acid derivative of formula (IV) to a Friedel-Crafts acylation, cleaving off one of the two substituents $R^1$ and separating the resulting salts of compounds of formula (I) from the salts of the isomeric compounds of formula (II) according to one of the processes described above.

The process of this invention is especially suitable for the manufacture of 4-hydroxy-3-methoxy-4'-methylbenzophenone, an intermediate for the manufacture of pharmaceutically active substances. Thus, 3,4-dimethoxy-4'-methylbenzophenone is obtainable by reacting veratrol and p-toluoyl chloride under Friedel-Crafts conditions. After cleavage of one methyl group, 4-hydroxy-3-methoxy-4'-methylbenzophenone can be separated from 3-hydroxy-4-methoxy-4'-methylbenzophenone by selective crystallization of the corresponding alkali salts. The details of this reaction are provided in Example 1 below.

Compounds of formula (I) can be further processed to pharmaceutically active compounds using a process of this invention. Thus, compounds of formula (I),

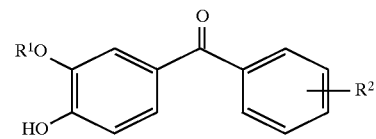   I wherein $R^1$ and $R^2$ are as defined above, obtained by means of the process described above, can be converted by adding a nitric acid, into compounds of formula (V),

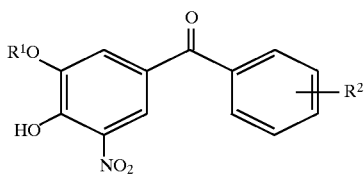   V wherein $R^1$ and $R^2$ are as defined above.

After demethylation, which converts $R^1$ to hydroxy, compounds of formula (VI) are obtained.

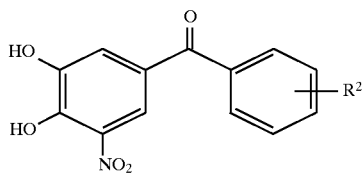   VI

Selective nitration in accordance with the process step described above is also well known and can be carried out in a solution containing aqueous nitric acid, for example, using 65% aqueous nitric acid, as described in Example 2. For the demethylation, which may be performed by standard methods for demethylation of an aromatic ether, the nitration product of general formula (V) can specifically be treated with a solution of aluminium trichloride in triethylamine and methylene chloride. After the reaction, the product, which can be liberated e.g. by acidic hydrolysis, can, for example, be extracted with methylene chloride and, if desired, purified further by recrystallization.

As set forth above, the compounds obtained in this manner are inhibitors of catechol-O-methyltransferase (COMT) and are suitable, for example, for the treatment of Parkinson's disease.

This process is especially suitable for the manufacture of 3,4-dihydroxy-4'-methyl-5-nitrobenzophenone. Thus, 4-hydroxy-3-methoxy-4'-methylbenzophenone can be obtained according to one of the processes described above and subsequently can be converted by selective nitration into 4-hydroxy-3-methoxy-4'-methyl-5-nitrobenzophenone. This compound is subsequently demethylated to 3,4-dihydroxy-4'-methyl-5-nitrobenzophenone.

Thus, this invention includes a process for producing compounds of formula (VI)

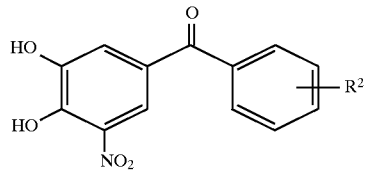

VI wherein $R^2$ is hydrogen, lower-alkyl or halogen, by combining a compound of formula (III),

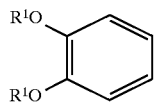

III wherein $R^1$ is as defined above,
with a reactive acid derivative of formula (IV)

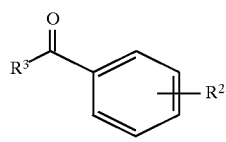

IV wherein $R^2$ is as defined above and $R^3$ is halogen, under conditions suitable for a Friedel-Crafts acylation, exposing the resulting product to conditions under which the substituent $R^1$ is cleaved off, to obtain a solution containing a mixture of salts of compounds of formula (I) and formula (II), adding a lithium or sodium salt to the mixture to crystallize the compound of formula (I), isolation the compound of formula (I) in crystalline form, separating the compound of formula (I) from the salt to obtain it in soluble form, adding nitric acid to obtain a compound of formula (V),

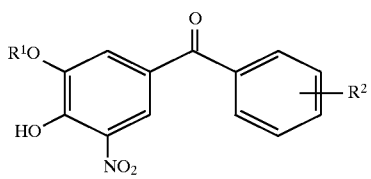

V wherein $R^1$ and $R^2$ are as defined above, and converting $R^1$ to hydroxy to obtain a compound of formula (VI),

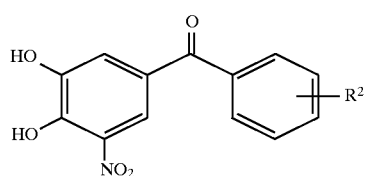

VI wherein $R^2$ is as defined above.

A preferred version of the above process is provided when the compound of formula (I) is 4-hydroxy-3-methoxy-4'-methylbenzophenone, the compound of formula (III) is 3-hydroxy-4-methoxy-4'-methylbenzophenone, the compound of formula (III) is veratrol, the compound of formula (IV) is p-toluoyl chloride, the compound of formula (V) is 4-hydroxy-3-methoxy-4'-methyl-5-nitro-benzophenone, and the compound of formula (VI) is 3,4-dihydroxy-4'-methyl-5-nitrobenzophenone.

The present invention relates to all aspects described above and especially to the use of the process for the manufacture of the compounds named above as well as to all compounds which are manufactured according to one of the said processes.

The following Examples serve exclusively to illustrate the invention and have no limiting character.

EXAMPLES

Example 1: Manufacture of 4-hydroxy-3-methoxy-4'-methylbenzophenone

Veratrol (pyrocatechol dimethyl ether, 1,2-dimethoxybenzene; 1.01 eq.) is dosed at 15°–25° C. and subsequently p-methylbenzoyl chloride (1.00 eq.) is dosed at 25°–30° C. into a suspension of aluminium trichloride (1.04 eq.) in methylene chloride, with 3,4-dimethoxy-4'-methylbenzophenone forming in a Friedel-Crafts acylation. After completion of the evolution of hydrogen chloride gas, aluminium trichloride is added in two portions (1.04 eq., 0.18 eq.) at intervals of 3 hours to the reaction mixture at 25°–28°. In order to complete the methyl ether cleavage, the reaction mixture is stirred at 32°–35° C. for a further 3–4 hours. The reaction mixture is cooled to 20° C. and stirred in a three phase mixture of dilute hydrochloric acid, methylene chloride and ice. The phases are separated. The aqueous phase is extracted with methylene chloride: The combined extracts are purified in succession with dilute hydrochloric acid and with water and finally washed with aqueous sodium bicarbonate solution.

The washed neutral methylene chloride phase is extracted with an about 1N aqueous potassium hydroxide solution (1.02 eq.), whereby the two isomeric hydroxymethoxybenzophenones are dissolved as potassium salts in the aqueous phase. The methylene chloride phase is separated. A saturated, aqueous sodium chloride solution is dosed into the aqueous phase. Thereby, the sodium salt of 4-oxy-3-methoxy-4'-methylbenzophenone crystallizes out, while the sodium or potassium salt of the isomeric 3-oxy-4-methoxy-4'-methylbenzophenone remains in solution.

The sodium salt of 4-oxy-3-methoxy-4'-methylbenzophenone is isolated, washed with dilute sodium chloride solution and subsequently dissolved in a two phase mixture of ethyl acetate and dilute hydrochloric acid. The aqueous phase is separated, the organic phase is washed with water, dried by azeotropic distillation, concentrated and filtered while hot. The filtered solution is cooled and treated with n-hexane, with the product crystallizing upon cooling. In order to complete the crystallization, the resulting suspension is stirred at −15° C. for 2 hours. The crystals are isolated and washed with a mixture of ethyl acetate/n-hexane and subsequently dried at 45°–55° C. in a vacuum. Yield of 4-hydroxy-3-methoxy-4'-methylbenzophenone: 50–64% of theory based on p-methylbenzoyl chloride used.

Example 2: Manufacture of 4-hydroxy-3-methoxy-4'-methyl-5-nitrobenzophenone

65% aqueous nitric acid (1.23 eq.) is dosed into a solution of 4-hydroxy-3-methoxy-4'-methylbenzophenone in glacial acetic acid at 20°–25° C. After stirring for 2 h. the resulting 4-hydroxy-3-methoxy-4'-methyl-5-nitrobenzophenone is precipitated by the addition of water. The crystals are isolated, washed with dilute acetic acid and subsequently with water. The product can be stored in water-moist form or in pre-dried form until it is used in the subsequent step (Example 3). Yield of 4-hydroxy-3-methoxy-4'-methyl-5-nitrobenzophenone: 80–87% of theory [based on] 4-hydroxy-3-methoxy-4'-methylbenzophenone used (dry weight basis).

Example 3: Manufacture of 3,4-dihydroxy-4'-methyl-5-nitrobenzophenone a) Demethylation of 4-hydroxy-3-methoxy-4'-methyl-5-nitrobenzophenone and isolation of 3,4-dihydroxy-4'-methyl-5-nitrobenzophenone as the crude product Water-moist 4-hydroxy-3-methoxy-4'-methyl-5-nitrobenzophenone is dried by azeotropic distillation with methylene chloride. A solution of aluminium trichloride (1.36 eq.) in triethylamine (5.30 eq.) and methylene chloride is dosed into the dried methylene chloride solution of 4-hydroxy-3-methoxy-4'-methyl-5-nitrobenzophenone at an internal temperature of 5°–15° C. Subsequently, the reaction mixture is boiled under reflux for at least 2.5 hours. As soon as the reaction has finished, the reaction mixture is cooled to 20°–25° C. and stirred into a two phase system consisting of methylene chloride and dilute hydrochloric acid of 0° C. The product liberated by the acidic hydrolysis is extracted with methylene chloride. The cooled methylene chloride extracts are washed with dilute hydrochloric acid and subsequently with water, filtered and concentrated in a vacuum. The distillation residue is dissolved in methylene chloride, filtered and subsequently concentrated. The concentrate is cooled, with the product crystallizing out. In order to complete the crystallization, the suspension is stirred at −15° C. for at least 3 hours. The crystals are isolated, washed with cold methylene chloride and stored in a methylene chloride-moist form until processed in the subsequent purification step.

b) Purification of 3,4-dihydroxy-4'-methyl-5-nitrobenzophenone (crystallization from ethanol/water 1:1 (v/v).

The methylene chloride-moist crude crystallizate is dissolved in abs. ethanol at 55°–65° C. and filtered while hot. The filtrate is concentrated, with the product beginning to crystallize. Water is dosed into the 50% (w/v) concentrate of 3,4-dihydroxy-4'-methyl-5-nitrobenzophenone/ethanol at 45°–55° C. such that a solvent mixture ethanol/water of 1:1 (v/v) results. In order to complete the crystallization, the suspension is cooled stepwise to −10° C. and is stirred at this temperature for at least 3 hours. The crystals are isolated, dried at 40° C. in a vacuum and subsequently micronized. Yield of 3,4-dihydroxy-4'-methyl-5-nitrobenzophenone: 72–85% of theory based on 4-hydroxy-3-methoxy-4'-methyl-5-nitrobenzophenone used.

I claim:

1. A process for the manufacture of benzophenone derivatives, which process comprises selective crystallization of a compound of formula (I),

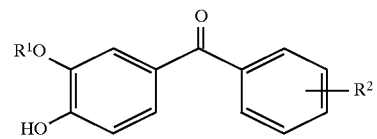

wherein $R^1$ is lower-alkyl and $R^2$ is hydrogen, lower-alkyl or halogen, from an aqueous solution containing a mixture of potassium salts of the compound of formula (I) and the compound of formula (II)

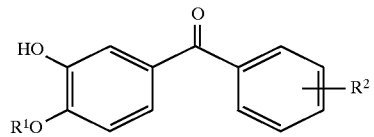

wherein $R^1$ and $R^2$ are as defined above; comprising
 a. adding a sodium or lithium salt to said mixture of potassium salts to crystallize the compound of formula (I); and
 b. isolating the compound of formula (I) in crystalline form as a sodium or lithium salt.

2. A process of claim 1, wherein $R^2$ is situated in the para-position.

3. A process of claim 1 wherein $R^1$ and $R^2$ are methyl.

4. A process of claim 1, wherein the salt is a sodium salt.

5. A process of claim 4, wherein the salt is sodium chloride.

6. A process of claim 1 which additionally comprises separating the compound of formula (1) in crystalline form from the sodium or lithium salt of formula

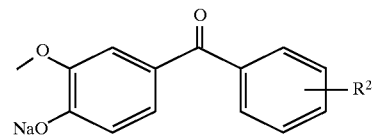

or

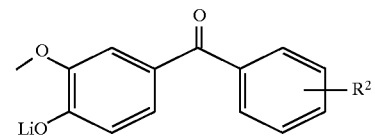

in order to obtain the compound of formula (1) in soluble form.

7. A process for making a compound of formula (I) in crystalline form where formula (1) is

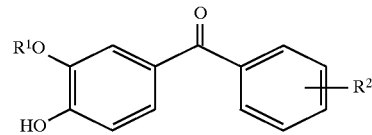

wherein $R^1$ is lower-alkyl and $R^2$ is hydrogen, lower-alkyl or halogen
which comprises:
 a. combining a compound of formula (III),

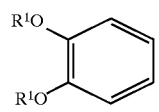

with a reactive acid derivative of formula (IV)

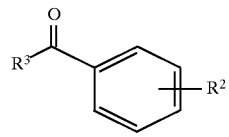

wherein $R^3$ is halogen, under conditions suitable for a Friedel-Crafts acylation;
 b. cleaving off the substituent $R^1$ by dealkylation in the presence of aluminum trichloride and extracting the product with a potassium salt, to obtain a solution containing a mixture of potassium salts of a compound of formula (I) and a compound of formula (II)

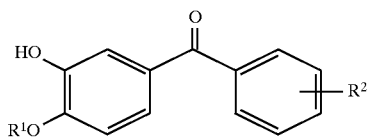

c. adding a lithium or sodium salt to the solution of step b to separate the compound of formula (I); and d. isolating the compound of formula (1) in crystalline form as a sodium or lithium salt.

8. A process of claim 7 which additionally comprises separating the compound of formula (1) in crystalline form from the sodium or lithium salt of the formula

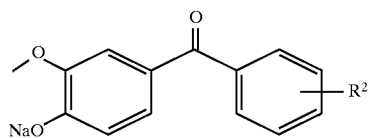

-continued or

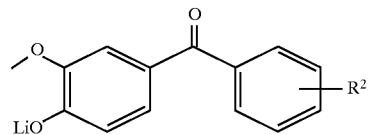

in order to obtain the compound of formula (I) in soluble form.

9. A process of claim 7 wherein aluminum trichloride is added in step a or step b or both.

10. A process of claim 7 wherein $R^3$ is chlorine.

11. A process of claim 7 wherein $R^1$ and $R^2$ are methyl and $R^2$ us un the para position, and $R^3$ is chlorine.

12. A process of claim 7 wherein the compound of the formula III is veratrol and the compound of formula IV is p-toluoyl chloride and the compound of formula (I) is 4-hydroxy-3-methoxy-4'- methylbenzophenone.

* * * * *

UNITED STATES PATENT AND TRADEMARK OFFICE
CERTIFICATE OF CORRECTION

PATENT NO. : 5,877,353
DATED : March 2, 1999
INVENTOR(S) : Jürg Bruhin

It is certified that error appears in the above-indentified patent and that said Letters Patent is hereby corrected as shown below:

IN THE CLAIMS:

Claim 3, Column 10, line 15: " $R^{1\ and\ R2}$ " should read --- $R^1$ and $R^2$ --- .

Claim 11, Column 12, line 18: " $R^2$ us un" should read --- $R^2$ is in --- .

Signed and Sealed this

Sixth Day of July, 1999

Attest:

Q. TODD DICKINSON

*Attesting Officer*    Acting Commissioner of Patents and Trademarks